United States Patent [19]

Gastrock

[11] 4,194,398
[45] Mar. 25, 1980

[54] SIGHT GLASS AND SAMPLING SYSTEM

[75] Inventor: Edward A. Gastrock, Metairie, La.

[73] Assignees: Charles L. Stewart, Glencoe, Ill.; Gastrock Protein Corporation, Metairie, La.

[21] Appl. No.: 960,095

[22] Filed: Nov. 13, 1978

Related U.S. Application Data

[62] Division of Ser. No. 721,203, Sep. 8, 1976, Pat. No. 4,139,646.

[51] Int. Cl.$^2$ .............................................. G01N 1/10
[52] U.S. Cl. ................................................ 73/422 TC
[58] Field of Search .......... 73/421 R, 421 B, 422 TC, 73/61.4; 116/276

[56] References Cited

U.S. PATENT DOCUMENTS

| | | | |
|---|---|---|---|
| 1,784,973 | 12/1930 | Preston | 73/421 |
| 1,837,858 | 12/1931 | Grace | 73/422 TC |
| 2,085,007 | 6/1937 | Conrath | 73/422 TC |
| 3,336,791 | 8/1967 | Malone | 73/422 TC |

*Primary Examiner*—S. Clement Swisher
*Attorney, Agent, or Firm*—Kinzer, Plyer, Dorn & McAchran

[57] ABSTRACT

A sight glass and sampling system for the output of a liquid processing device. The system includes a sight glass connected to the outlet of a liquid processing device. A first three-way valve controls the flow from the outlet of the liquid processing device to the inlet of the sight glass. A second three-way valve controls the outlet from the sight glass. A valve controlled sample conduit is connected between the first and second three-way valves. A bypass conduit connects the first and second three-way valves and is controlled by these valves.

3 Claims, 2 Drawing Figures

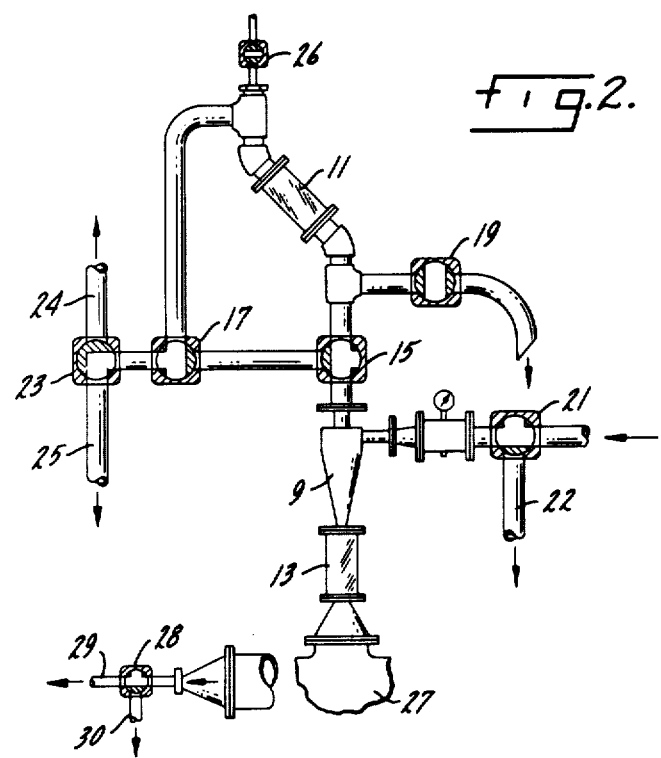

SIGHT GLASS AND SAMPLING SYSTEM

This is a division of application Ser. No. 721,203, filed Sept. 8, 1976, now U.S. Pat. No. 4,139,646.

SUMMARY OF THE INVENTION

This invention relates to a sight glass and sampling system for the output of a liquid processing device. It provides continuous visual examination of the overflow stream and the under flow stream from a liquid cyclone separator. Changes in the appearance and behavior of these streams as viewed in the overflow sight glass and underflow sight glass will signal to the operator a possible need for changing the operating feed, pressure, split ratio, etc. of the run. The overflow sight glass may be isolated from the system so that a sample may be withdrawn for analysis or for any other purpose without disturbing the system.

BRIEF DESCRIPTION OF THE DRAWINGS

FIG. 2 is an elevational view of a sampling arrangement for the cyclone separators of my invention.

THE PROCESS OF THE PRESENT INVENTION

Figure 1:
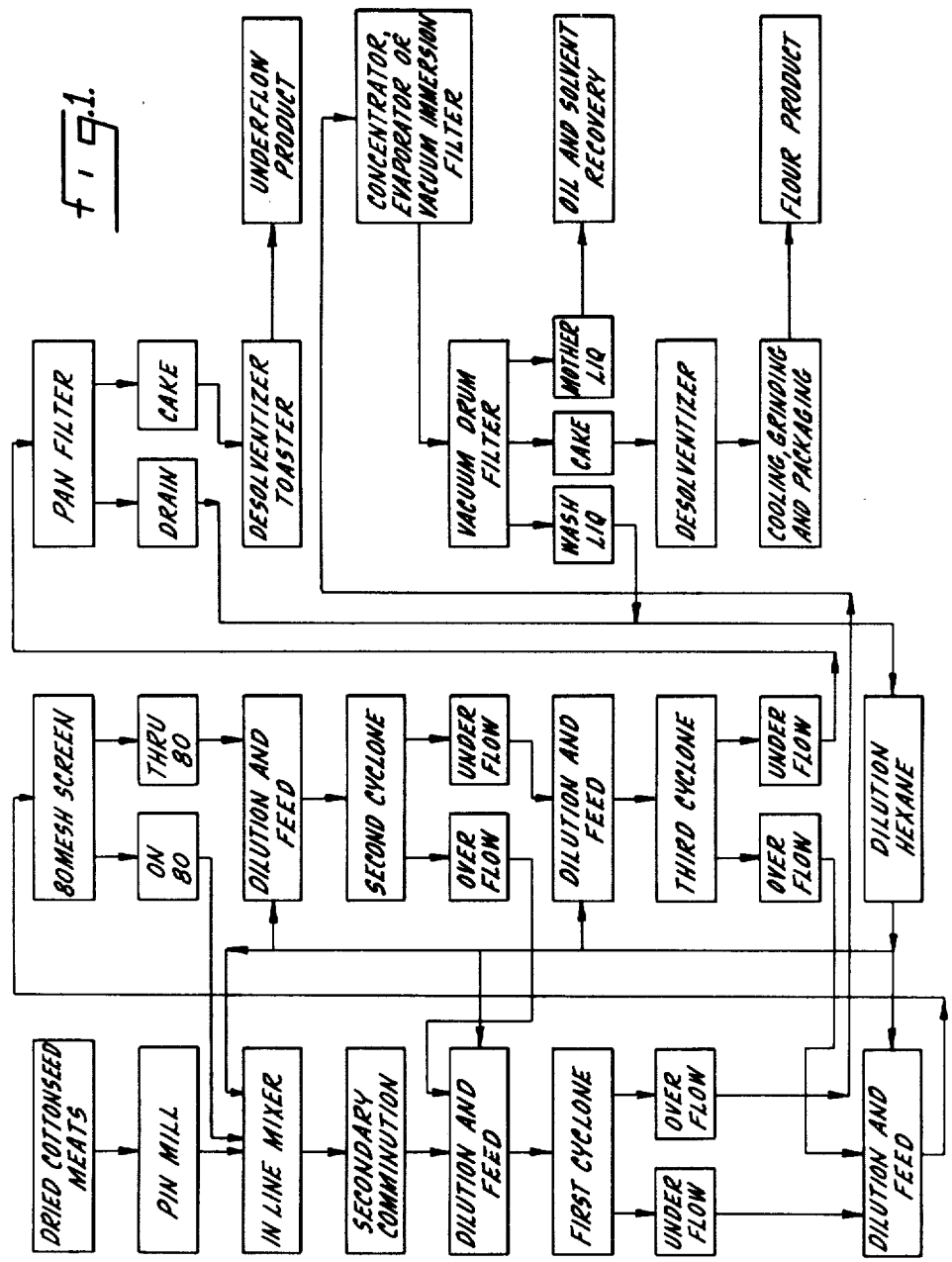
FIG. 1 is a flow sheet showing the process of my invention.

The process of this invention will produce a high-grade protein concentrate, the quality of which will be evidenced by its representative analysis as follows:

Composition:
Moisture, %: up to 3.7,
Protein (Nitrogen×6.25) MFB%: 65 or more,
Nitrogen, %: 10.4 or more,
Nitrogen solubility (in 0.02 N NaOH) %: up to 99,
Total gossypol, %: up to 0.18,
Free gossypol, %: up to 0.04,
Lipids, %: up to 1.0,
Crude fiber, %: 2.4,
Ash, %: 7.54,
E.A.F. Lysine (g./16 g N): up to 3.94,
Residual Hexane (ppm): up to 25.

The above-listed compositional analysis is possible of achievement by reason of new discoveries that relate to the handling, preparation, and drying of the cottonseed kernels; by the discovery of new continuous techniques (refer to FIG. 1) in the application of equipment for selective and progressive comminution of the cottonseed kernels using initial dry pin milling followed by secondary milling in slurry form with recycling whereby the pigment glands are freed essentially intact from their enrobing tissue, and the protein meal particles are finely comminuted without rupturing the pigment glands; by the discovery of a highly efficient, rapid and continuous solvent process using three 3-inch diameter liquid cyclones in series whereby a concentrated pigment gland fraction for diversion from the process is obtained as the underflow from the third 3-inch liquid cyclone, the overflow obtained from the first 3-inch liquid cyclone being employed directly to produce a product of 65 percent or higher by weight protein content and at a yield of 50 percent or higher based on the total solids fed to the first cyclone; by the discovery of a highly efficient continuous process whereby the coarse meal underflow fraction from the first cyclone is diluted with the overflow fraction from the third cyclone, the resulting slurry mixture is passed to a continuously operating screen (approximately 80 mesh), the slurry passing through the screen serving as feed to the second 3-inch cyclone and the coarse meal retained on the screen being returned to the in-line mixer receiving the comminuted feed from the pin mill and the mixed slurry from the in-line mixer being passed through a second comminuting device and diluted with overflow slurry from the second 3-inch cyclone, such diluted slurry serving as feed to the first cyclone, the overflow of which contains all of the purified fine cottonseed flour (50% or more of the solids fed to the process) which is the product of the process, after concentrating, filtering and washing with hexane to remove oil; desolventizing and packaging. The underflow slurry from the third cyclone is pumped to a horizontal vacuum filter, drained and washed, if necessary, with commercial n-hexane, desolvenitized, cooled and packaged.

To prevent or minimize the concurrent rupture of pigment glands, it is essential first to dry the cottonseed kernel meats to a maximum of 2.5 percent by weight moisture.

The next step is one of the most important in the process. With insufficient size reduction, the yield of high-protein flour will be low; with excessively rough comminution, the pigment glands will be ruptured or overly fragmented thereby reducing the efficiency of the cyclone to separate them from the product flour. A sieveless, wide-chamber pin mill was found to be acceptable for the initial comminution step. The selected mill has two contra-rotating discs with rings of intermeshing round pins. The discs operate separately from the mill side and from the door. The proper degree of disintegration, with minimum gland rupture, can be accomplished if the mill side pin disc is operated at 9,500 RPM and the door side pin disc at 2,500 RPM. It is essential that the meats be dried to a maximum of 2.5 percent by weight of moisture content, and they should be unextracted prior to the comminution step.

The milled meats are next fed to an in-line mixer into which the oversize material from the 80 mesh screen is also fed, together with the necessary quantity of dilution hexane to yield a resulting slurry with a consistency of approximately 50 percent total solids.

I have discovered that it is highly beneficial to maintain the oil content of the cottonseed meats as high as practical in the comminuting steps. This is accomplished in the initial comminution step by using unextracted meats. In the second comminution step, it is accomplished by maintaining the oil content of the miscella associated with the slurry in the second comminution step at as high a value as is practical. To this end, the wash liquor from the vacuum drum filter and the mother liquor and wash liquor from the horizontal pan filter are returned to the dilution tank, mixed with commercial n-hexane as needed and used for dilution throughout the system where needed and as needed. The mother liquor from the vacuum drum filter contains all of the oil leaving the process. This mother liquor miscella is pumped to standard oil and solvent recovery equipment; the oil is pumped to tanks and the recovered hexane is returned to the process.

I have found that the under-flow from each cyclone as it progresses from the first cyclone to the third or last cyclone progressively contains a smaller and smaller proportion of purified fine flour. Thus, this fine flour gradually and eventually counter currently finds its way to the overflow of the first cyclone and is eventually recovered as part of the yield of purified fine flour from the process, thus exalting the yield.

Concurrently, the oil percent of the miscella associated with each underflow as it progresses from the first cyclone to the third or last cyclone becomes progressively lower so that eventually as the underflow from the third cyclone is pumped to the horizontal pan filter, the drained cake from the pan filter requires little or no washing with commercial n-hexane.

It may be found advantageous to use four or more cyclones in series rather than three cyclones. Such a changed flow could be easily accomplished. It is also obvious that two or more lines in parallel, each of which has three or more cyclones, could be used to multiply the capacity of the plant.

The slurry from the secondary comminution at about 50% total solids is diluted with the overflow from the second cyclone plus dilution hexane to a consistency of about 22% total solids and then pumped at a pressure of about 40 pounds per square inch into the tangential feed port of the first liquid cyclone at its largest diameter. The resulting centrifugal action whirls the feed stream around the periphery of the interior of the cyclone and exerts a centrifugal force of approximately 5000 times the force of gravity, depending on the pressure and rate of feed of the slurry material. This centrifugal action causes the larger, heavier, and more compact particles having the lowest ratio of surface area to mass (as typified by the ovoid-shaped pigment glands and the larger particles of meat tissue) to travel rapidly to the peripheral wall of the liquid cyclone. These particles which include essentially all of the pigment glands, the larger meats particles, and hull particles, are forced by the moving liquid down the tapered sides of the cyclone to the lower constrictive tip or "apex" of the cyclone where they are discharged, together with a minor portion of the solvent, as underflow. The finer meal particles or flour, which are essentially free of pigment glands and are of lower effective specific gravity and lower differential settling rate than the pigment glands and coarse meal particles due to their relatively high ratio of surface area to mass, move much more slowly towards the peripheral wall of the liquid cyclone and are forced upwards by the moving liquid through the vortex finder at the center of the cyclone and are discharged through the vortex finder at the top as overflow.

The underflow stream ranges in solids content from about 30 percent to about 45 percent by weight while the overflow stream ranges in solids content from about 10 percent to about 15 percent by weight, with the overflow stream amounting to from about 50 percent to about 90 percent and higher by weight of the feed stream, while the underflow stream amounts to from about 10 percent to about 50 percent of the weight of the feed stream. The ratio by weight of the overflow stream to that of the underflow stream and the solids content of the respective streams is controlled by the rate and pressure at which the feed stream enters the tangential feed port of the liquid cyclone, the cross-sectional area of the "apex" orifice through which the underflow discharges, the makeup of the solids content of the feed stream with respect to particle size, and the solids content of the feed stream. The larger, and more compact particles of the slurry which include the bulk of the pigment glands, are forced by the moving liquid down the tapered sides of the "apex", or small lower end where they are discharged as underflow (UF). The finer meal particles, practically free of pigment glands, are forced to the center of the cyclone and are discharged upward through the vortex finder as the overflow (OF). The cyclone split or weight ratio of OF to UF is controlled by adjusting the speed of a positive displacement progressing cavity UF slurry pump which is located at the "apex" or UF opening of the cyclone. The "split" may also be controlled by varying the "apex" orifice. The "split" ratio is normally from approximately 1 to 1 to approximately 9 to 1. Under certain conditions, smaller or larger splits may be desirable.

Liquid cyclones are available in many sizes, usually designated by the maximum inside diameter of the cylindrical portion, expressed in inches (in.). The cyclone used in this invention is a 3 inch cyclone. This invention is not limited to the use of this size cyclone because other liquid cyclones, larger and smaller can be used.

It should be noted that the capacity of the system may be greatly expanded by the use of multiple lines of liquid cyclones in parallel.

The OF from the first liquid cyclone, having a solids content of about 14 percent is suitable as feed to a continuous vacuum drum filter. Filter runs on a small vacuum drum filter have yielded a rate of above 3.5 pounds of solids per square foot of filter area per hour. During filtration, it was observed that the filter cake had a tendency to crack which resulted in ineffective lipid removal. It was discovered that this problem could be solved by use of a feed slurry wash of the cake as it emerged from the slurry tank.

Commercial wiped film evaporators are available to concentrate the feed to the vacuum drum filter. Concentration of the feed to the vacuum drum filter would greatly reduce the size of the filter necessary for satisfactory operation.

A further advantage of increasing the feed to the filter would be a reduction in the tendency of ultra fine flour in the slurry feed to the filter to pass through the filter cloth thus reducing difficulties in the handling and processing of the mother liquor and wash liquor from the vacuum drum filter.

CLASSIFICATION BY LIQUID CYCLONES

The discharge from the secondary comminuting unit is diluted in the first cyclone feed tank which is maintained under sufficient agitation to keep all solids in uniform suspension and is fed to the first three inch diameter liquid cyclone at 35–45 p.s.i. pressure by a progressive cavity pump. Classification and separation of the suspended particles in the slurry takes place in the liquid cyclone to deliver an underflow and an overflow stream. The under-flow discharges from the lower tip, or "apex" of the liquid cyclone. The underflow amounts to between ten percent and fifty percent of the total slurry entering the feed aperture of the liquid cyclone and contains from about thirty percent to forty-five percent of solids. The overflow discharges from the upper, or the vortex finder outlet of the cyclone. This overflow stream amounts to from about fifty percent to about ninety percent of the total slurry entering the feed aperture of the cyclone and contains from about ten percent to fifteen percent of solids. The weight ratio of overflow to underflow is defined as the "split" and preferably ranges between from one part of overflow to one part of underflow to nine parts of overflow to one part of underflow.

The split ratio is controlled primarily by adjusting the speed of a positive displacement underflow slurry pump which is located at the apex opening of the cyclone. The solids contents of the overflow and underflow streams are also controlled by the split ratio and are affected by the percentage of solids in the feed stream and the degree of fineness of the solids.

The underflow contains essentially all of the intact and fractured pigment glands of the feed slurry, relatively coarse (but smaller than 80 mesh) particles of meats many of which contain embedded pigment glands and hull particles. These solids range from one percent to four percent in gossypol content and from forty-four percent to fifty-nine percent in protein.

SAMPLING PROCEDURES

FIG. 2 of the drawings shows a piping arrangement that provides continuous visual examination of the overflow stream and the underflow stream from a liquid cyclone separator 9 of the type used in my process. Changes in the appearance and behaviour of these two streams as seen in overflow sight glass 11 and underflow sight glass 13 will signal to the operator a possible need for changing the operating feed, pressure, split, etc. on the run. In addition, the overflow sight glass 11 may be isolated from the system by suitably setting three-way valves 15 and 17. When this is done, a sample may be withdrawn from sight glass 11 for analysis or for any other purpose by opening valve 19 without disturbing the system. The piping is arranged so that sight glass 11 is inclined at 45° rather than vertical permitting the operator to observe the settling characteristics of the particles in the sight glass without withdrawing the samples.

Three-way valve 21 controls flow to the cyclone from the cyclone feed pump and can return the flow through pipe 22 to the feed tank. Two-way valve 23 controls overflow from the cyclone between overflow pipe 24 and feed tank return pipe 25. Valve 26 controls an air vent. Underflow pump 27 discharges through valve 28 which directs flow to either the underflow pipe 29 or feed tank return pipe 30.

This arrangement of piping is applicable to all of the cyclones of my process and provides for shifting of OF and UF streams between source and destination at start-up and in emergency situations and will provide continuous visual evidence of cyclone performances. This piping arrangement may be modified for slurry lines other than around the cyclones.

I claim:

1. A sight glass and sampling system for the output of a liquid processing device including:
   a sight glass connected to the outlet of said liquid processing device.
   a first three-way valve controlling the flow from the outlet of said liquid processing device to the inlet of said sight glass,
   a second three-way valve controlling the outlet from said sight glass,
   a valve controlled sample conduit connected between said first and second three-way valves, and
   a by-pass conduit connecting said first and second three-way valves and controlled by said valves.

2. The piping arrangement of claim 1 in which said sight glass is inclined to the vertical.

3. The piping arrangement of claim 2 in which said sight glass is inclined at an angle of 45° to the vertical.

* * * * *